(12) United States Patent
Su et al.

(10) Patent No.: US 9,068,050 B2
(45) Date of Patent: Jun. 30, 2015

(54) BRIDGED BIS(ALKOXYSILANE) OR SILSESQUIOXANE COMPOUND HAVING BENZOXAZINE-CONTAINING GROUP

(75) Inventors: Wen-Chiung Su, Taipei (TW); Ying-Ling Liu, Taoyuan County (TW)

(73) Assignee: CHUNG-SHAN INSTITUTE OF SCIENCE AND TECHNOLOGY, ARMAMENTS, BUREAU, MINISTRY OF NATIONAL DEFENSE, Taoyuan County (TW)

( * ) Notice: Subject to any disclaimer, the term of this patent is extended or adjusted under 35 U.S.C. 154(b) by 498 days.

(21) Appl. No.: 13/222,015

(22) Filed: Aug. 31, 2011

(65) Prior Publication Data

US 2013/0053529 A1    Feb. 28, 2013

(51) Int. Cl.
| | | |
|---|---|---|
| C08G 77/04 | (2006.01) |
| C08G 77/52 | (2006.01) |
| C07F 7/08 | (2006.01) |
| C07F 7/18 | (2006.01) |
| C08G 77/54 | (2006.01) |

(52) U.S. Cl.
CPC .............. *C08G 77/52* (2013.01); *C07F 7/0854* (2013.01); *C07F 7/1836* (2013.01); *C08G 77/54* (2013.01)

(58) Field of Classification Search
CPC ..... C07F 7/0854; C07F 7/1836; C08G 77/52; C08G 77/54
USPC .......................................................... 528/25
See application file for complete search history.

(56) References Cited

FOREIGN PATENT DOCUMENTS

| CN | 101750896 | * | 6/2010 |
| CN | 102 134 254 | * | 7/2011 |

OTHER PUBLICATIONS

CN 102 134 254 Abstract (2011).*
Liu, et al., Self-assembled benzoxazine-bridged polysilsesquioxanes exhibiting ultralow-dielectric constants and yellow-light photoluminescent emission, Journal of Materials Chemistry, Apr. 11, 2011, 21, 7182.

* cited by examiner

*Primary Examiner* — Kuo-Liang Peng
(74) *Attorney, Agent, or Firm* — Jackson IPG PLLC; Demian K. Jackson (57) ABSTRACT

A benzoxazine-bridged compound is provided. The compound has a low dielectric constant, a high mechanic strength and a high glass transition temperature. The compound has a highly cross-linked structure with a yellow-light photoluminescent emission. Characterization of the present disclosure has been conducted with Fourier transform infrared, nuclear magnetic resonance, molecular mass and elemental analysis.

2 Claims, 12 Drawing Sheets

BRIDGED BIS(ALKOXYSILANE) OR SILSESQUIOXANE COMPOUND HAVING BENZOXAZINE-CONTAINING GROUP

TECHNICAL FIELD OF THE DISCLOSURE

The present disclosure relates to a bridged compound; more particularly, relates to a self-assembled bridged alkoxysilane structure having benzoxazine.

DESCRIPTION OF THE RELATED ARTS

Following the development of chip technologies, demands on a materials having low dielectric constants (k<2.0) are increasing. Porous materials may contain some air in its solid network structure and so have k values lower than 2.0. However, the introduction of porous materials into dielectric material applications may result in sacrificing part of the properties of the dielectric materials and bring in new challenges to chip fabrication procedure. Hence, sol-gel method is tried to be used in fabricating hybrid organic-inorganic materials. Mechanical properties of the dielectric material can be enhanced through improving film network connectivity of hybrid organic-inorganic materials. A preferred choice is found in using carbon-bridged alkoxysilane as precursors. Organic groups are introduced into the dielectric materials through sol-gel to reduce friability. Specific porogens may help controlling sizes and distribution of pores. Mutually-connected networks and controlled closed nanopores may help maintaining the mechanical properties of the dielectric materials and reducing their k values.

Bridged polysilsesquioxanes could be obtained using carbon-bridged bis(alkoxysilane) as precursors. The chemical structures of the carbon-bridging groups play key roles in the structure, morphology, and mechanical properties of the resulting gel products. Periodic mesoporous organosilica (PMO) materials with integration of bridging organic groups into the channel walls may be fabricated by self-assembly of silsesquioxane precursors. The dielectric constants of the hybrid films decrease with the increasing of the organic portions. The dielectric constant of the hybrid film will be decreased following the increasing of the organic part in the structure. Dielectric materials made of neat bridged polysilsesquioxanes display dielectric constants of about 2.9. Thermal treatments at around 400° C. cause bridging-to-thermal transformation to the bridged polysilsesquioxanes and further reduce their k values to about 1.8. Further improvements of the dielectric constants of the fabricated materials may be achieved by more control of structural phases.

Structural control of bridged silsesquioxanes has been reported. The materials have controlled morphologies in different sizes and shapes. It is noteworthy that the dielectric constants of composite materials depend not only on the inorganic filler compositions but also on the orientation of the fillers. The orientation of the low-k fillers into layer structures, which are perpendicular to the applied electrical field, would result in the dielectric constants of composites being close to the dielectric constant of the low-k filler over a wide range of the filler contents. Hence, the orientation of the low-k components in the organic/inorganic composites is an effective approach for fabricating low-k materials. Thus, self-assembled bridged polysilsesquioxanes, which have layer structures perpendicular to the applied electrical field, is an approach under development for fabricating low-k materials.

Hence, the prior arts do not fulfill all users' requests on actual use.

SUMMARY OF THE DISCLOSURE

The main purpose of the present disclosure is to provide a bridged alkoxysilane compound with a low dielectric constant and a high mechanical strength.

The second purpose of the present disclosure is to provide the compound through a clean and simple self-assembly reaction for saving cost.

The third purpose of the present disclosure is to reduce a dielectric constant of the compound through increasing its porosity.

The fourth purpose of the present disclosure is to reduce the dielectric constant of the compound through controlling phases and ratios of organic groups in the compound.

The fifth purpose of the present disclosure is to effectively improve a mechanical strength of the compound through forming a cross-linked film network structure in the compound.

The sixth purpose of the present disclosure is, through intermolecular and intramolecular hydrogen bonds, to effectively induce the self-assembled cross-linked network structure and to further maintain a film structure of the compound.

The seventh purpose of the present disclosure is to obtain an electro-luminescent property by adding an electro-luminescent group into an organic bridging group of the compound.

To achieve the above purpose, the present disclosure is a bridged bis(alkoxysilane) or silsesquioxane compound having a benzoxazine-containing group, where the compound has a general structural formula as follows:

where X is a chemical bond, —O—, —CH$_2$—, where R$^1$ and R$^3$ are two constituent selected from two of the same constituent and two different constituents; where each of $R^1$ and $R^3$ is selected from $C_1$-type to $C_8$-type alkyl groups and $C_6$-type to $C_{15}$-type aryl groups; and where m is an integer bigger than zero. Accordingly, a novel bridged bis (alkoxysilane) or silsesquioxane compound having a benzoxazine-containing group is obtained.

BRIEF DESCRIPTIONS OF THE DRAWINGS

The present disclosure will be better understood from the following detailed description of the preferred embodiment according to the present disclosure, taken in conjunction with the accompanying drawings, in which.

DESCRIPTION OF THE PREFERRED EMBODIMENT

The following description of the preferred embodiment is provided to understand the features and the structures of the present disclosure.

Please refer to FIG. 1A to FIG. 6C, which are views showing FTIR spectrums, a $^1$H NMR spectrum and a $^{29}$Si NMR spectrum of Bz-BES; a view showing solid 29Si NMR spectrums of XG-Bz-BES and PBz-BPSSQ; a view showing DSC thermal spectrums of Bz-BES, XG-Bz-BES and PBz-BPSSQ; views showing nitrogen adsorption/desorption isotherms of XG-Bz-BES and PBz-BPSSQ; views showing TEM micrographs of PBz-BPSSQ and PBz-BPSSQ/PBz; and views showing a first, a second and a third reactions on fabricating the present disclosure. As shown in the figures, the present disclosure is a bridged bis(alkoxysilane) or silsesquioxane compound having a benzoxazine-containing group, where the compound has a first general structural formula as follows:

X is a chemical bond, —O—, —CH$_2$—, and $R^3$ are two of the same constituent or two different constituents; each of $R^1$ and $R^3$ is a group selected from $C_1$-type to $C_8$-type alkyl groups and $C_6$-type to $C_{15}$-type aryl groups; and m is an integer bigger than zero.

When m is 1, the compound having the first general structural formula has a specific structural formula as follows:

where $R^2$ and $R^4$ are two of the same constituent or two different constituents; and each of $R^2$ and $R^4$ is a group selected from $C_1$-type to $C_8$-type alkyl group.

The compound having the first general structural formula may have another specific structural formula as follows:

where m is an integer bigger than 0.

The compound having the first general structural formula may have another specific structural formula as follows:

The compound may have a second general structural formula as follows:

where X is a chemical bond, —O—, —CH$_2$—, $R^1$ and $R^3$ are two of the same constituent or two different constituents; each of $R^1$ and $R^3$ is a group selected from C$_1$-type to C$_8$-type alkyl groups and C$_6$-type to C$_{15}$-type aryl groups; and each of m and n is an integer bigger than zero.

The compound having the second general structural formula may have a specific structural formula as follows:

[Synthesis Processes]

The present disclosure uses the following materials: bisphenol-A (BPA) from Showa chemical industry company; methanal (37% water solution) and 3-aminopropyl-triethoxysilane from Aldrich chemical industry company; and, tetrahydrofuran (THF) from Tedia chemical industry company. The above materials are all dried through molecular sieves before using.

First State-of-Use: Fabricating Bz-BES Having Benzoxazine Group

Figure 6A:
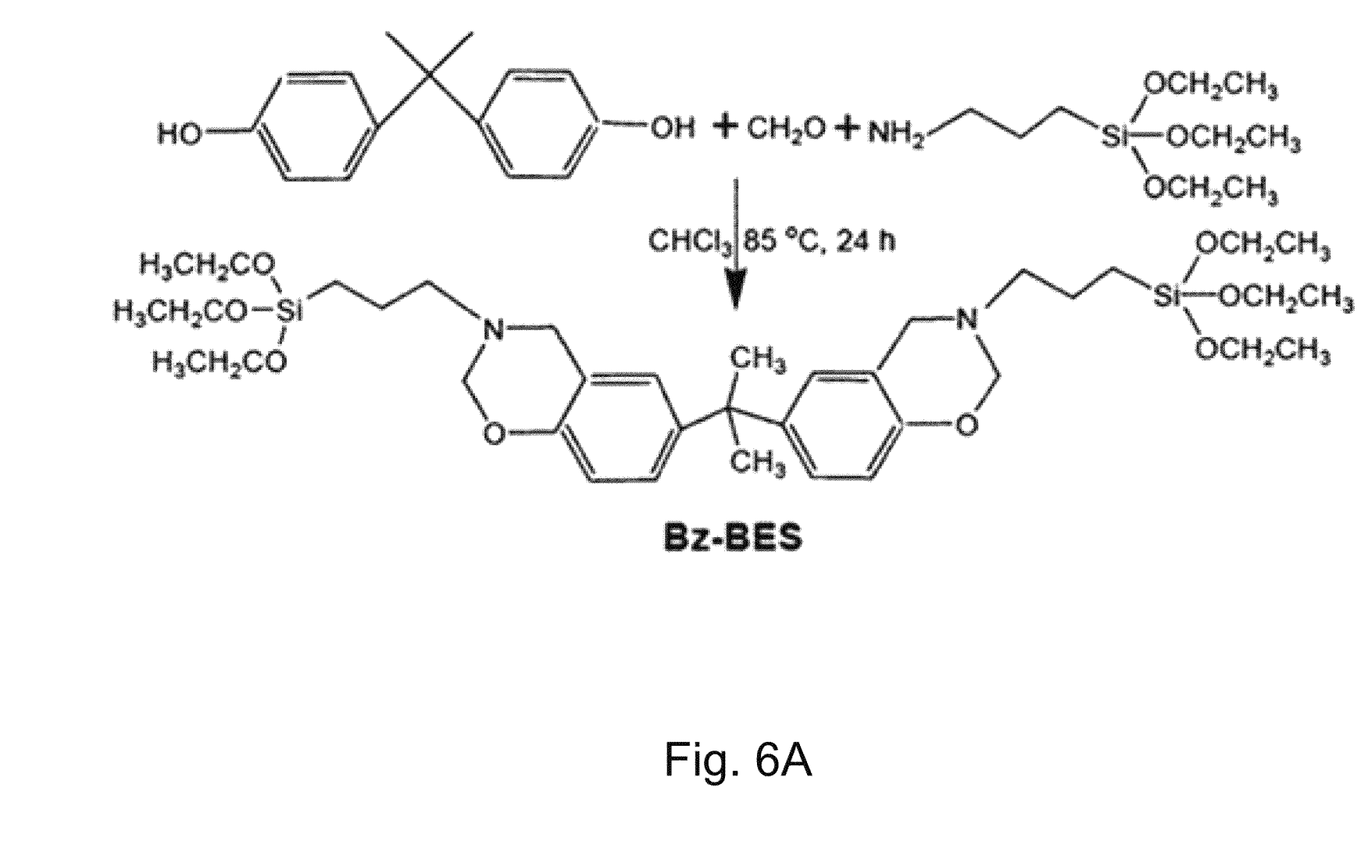
FIG. 6A is the view showing the first reaction on fabricating the present disclosure.

In FIG. 6A, BPA (10 g, 43.8 mmol), methanal (5.26 g, 175 mmol) and 3-aminopropyl-triethoxysilane (19.4 g, 87.6 mmol) are mixed in chloroform (100 mL) for reaction at 85 Celsius degrees (° C.) for 24 hours (hr). The product obtained after the reaction do not need to be further purified. The product is directly condensed to obtain an anticipated product Bz-BES (yield: 75%). Elemental analysis calcd (%) for C$_{37}$H$_{62}$N$_2$O$_8$Si$_2$: C 61.83, H 9.63, N 3.89; found C 61.70, H 8.67, N 3.81.

Second State-of-Use: Hydrolyzing and Condensing Bz-BES Having Benzoxazine Group

Figure 6B:
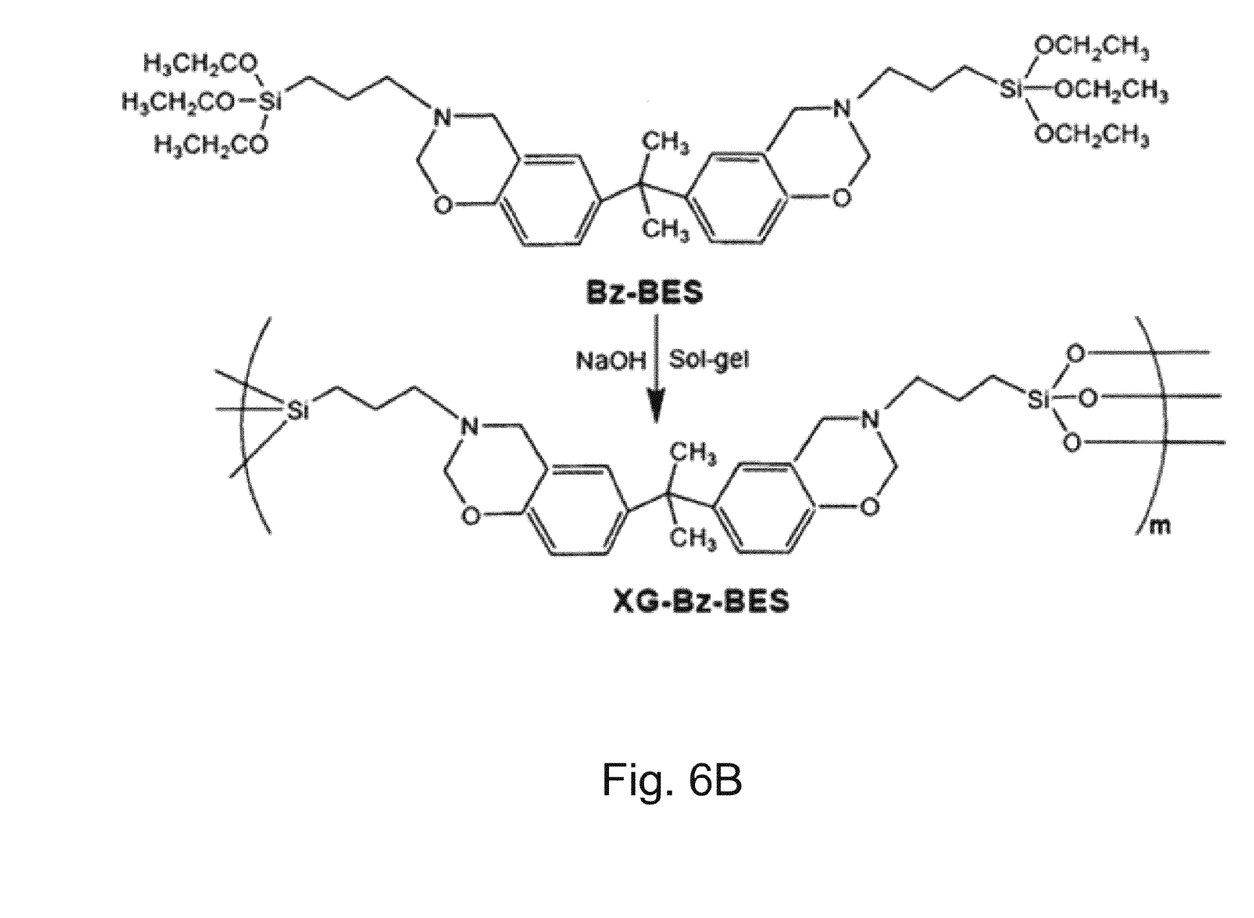
FIG. 6B is the view showing the second reaction on fabricating the present disclosure.
Figure 6C:
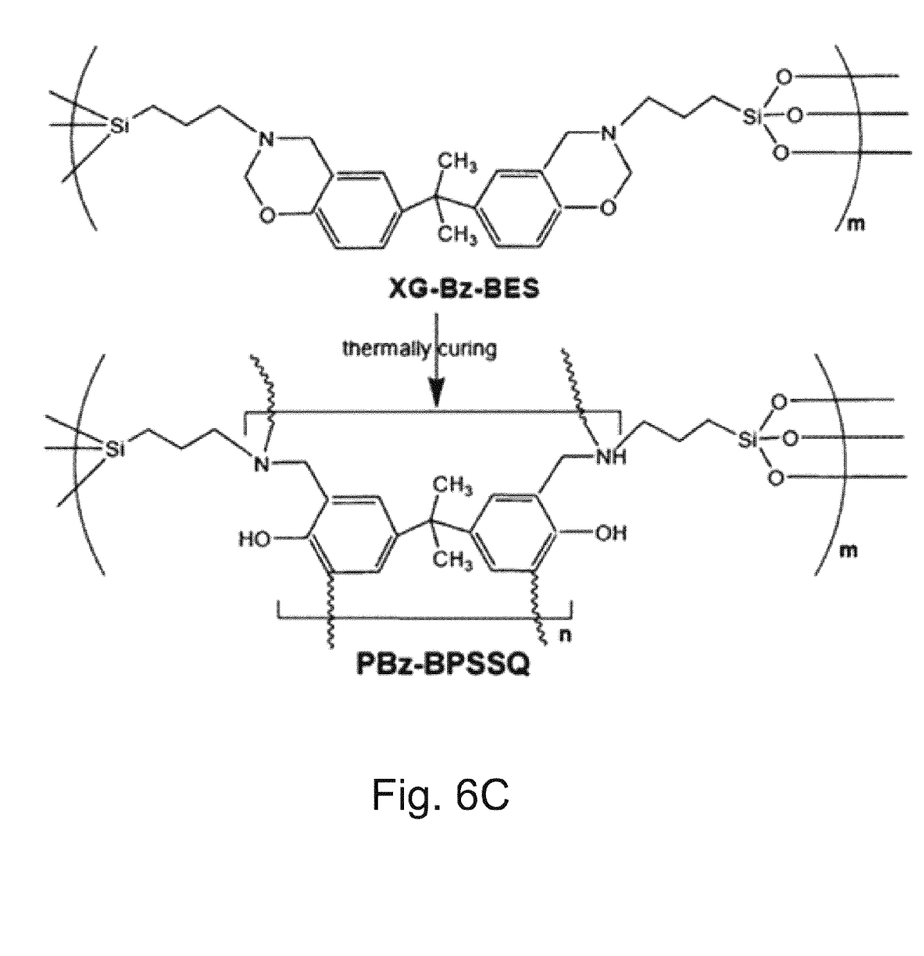
FIG. 6C is the view showing the third reaction on fabricating the present disclosure.

In FIG. 6B, Bz-BES is dissolved into THF to obtain a THF solution having a 0.4 density. The THF solution having Bz-BES is mixed with an NaOH water solution having a 1.08N density for reaction. In the mixed solution thus obtained, a molar ratio of water/Bz-BES is about 6.2. After the reaction is processed at 30° C. for 48 hrs for the mixed solution, a gel product is obtained. After the gel product is washed with THF and distilled water and is vacuum dried at a room temperature, a xerogel product of Bz-BES (XG-Bz-BES) is obtained.

Third State-of-Use: Fabricating PBz-BPSSQ Having Benzoxazine Group Through Thermal Treatment In FIG. 6C, the Bz-BES-containing THF solution having a 0.4M density is mixed with the NaOH water solution having a 1.08N density for reaction. After reacting at 30° C. for 2 hrs, the mixed solution is pulled into a stainless mold. Then, the mixed solution is thermally cured at 90° C. for 1 hr, at 150° C. for 1 hr, at 180° C. for 3 hrs and at 220° C. for 2 hrs. Thus, a polysilsesquioxanes product having benzoxazine group (PBz-BPSSQ) is obtained through thermal treatment.

A nanocomposite of polybenzoxazine/PSSQ can be obtained through the above processes too. What differs in between is that the starting materials for reactions are Bz- BES and BPA-FBz (with a weight percents of 50/50%); and the obtained product is coded as PBz-BPSSQ/PBz.

Figure 1A:
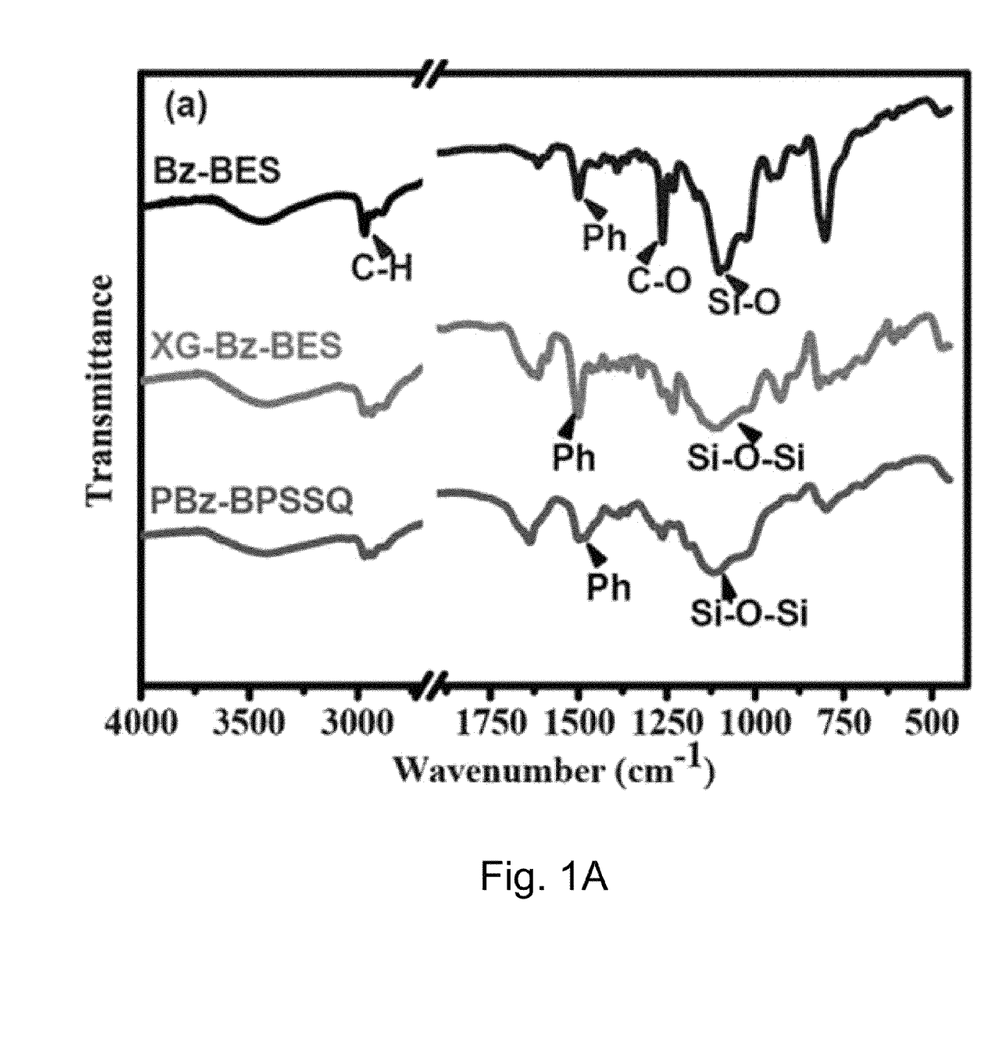
FIG. 1A is the view showing the FTIR spectrums of Bz-BES.
Figure 1B:
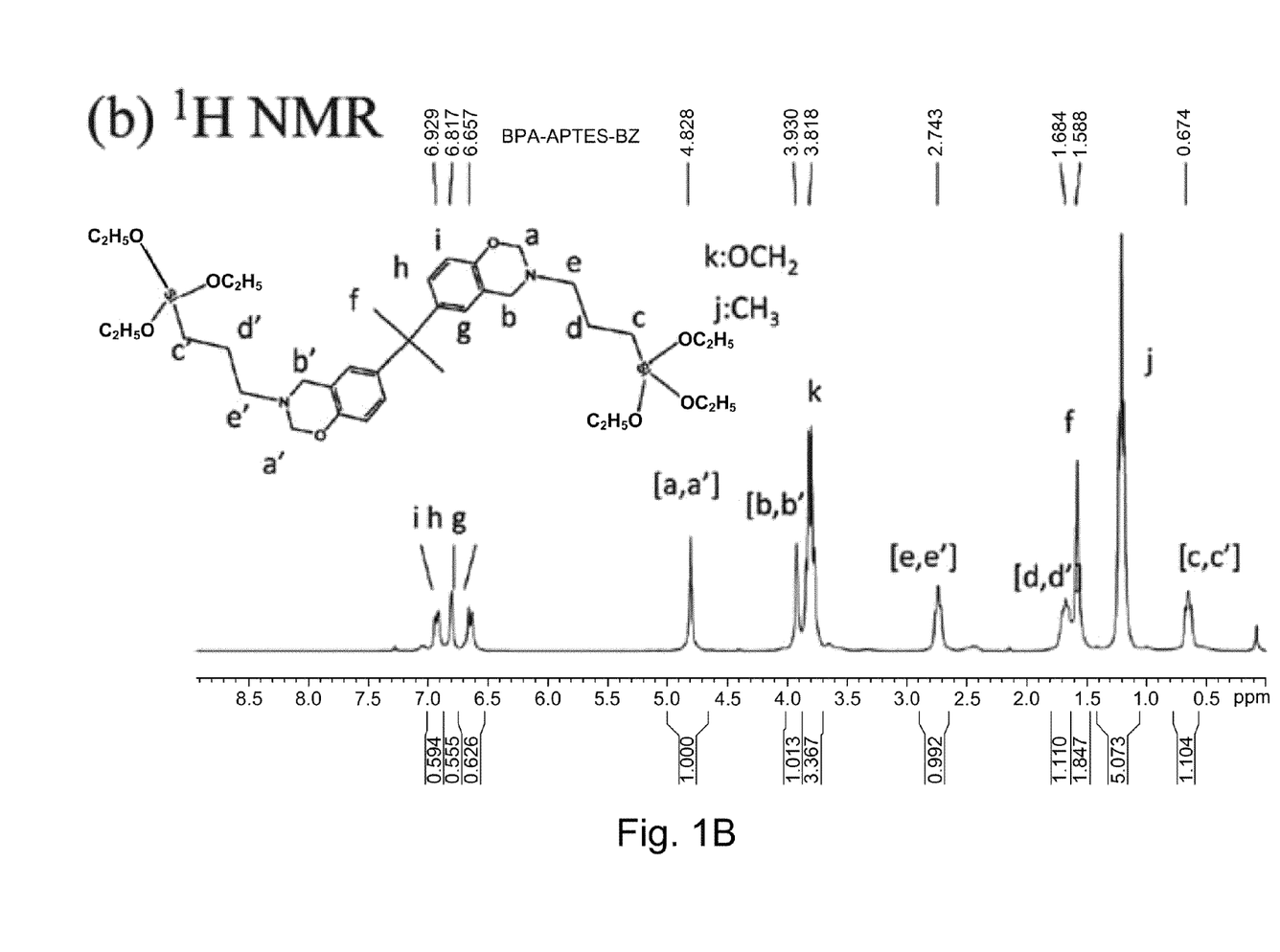
FIG. 1B is the view showing the $^1$H NMR spectrum of Bz-BES.
Figure 1C:
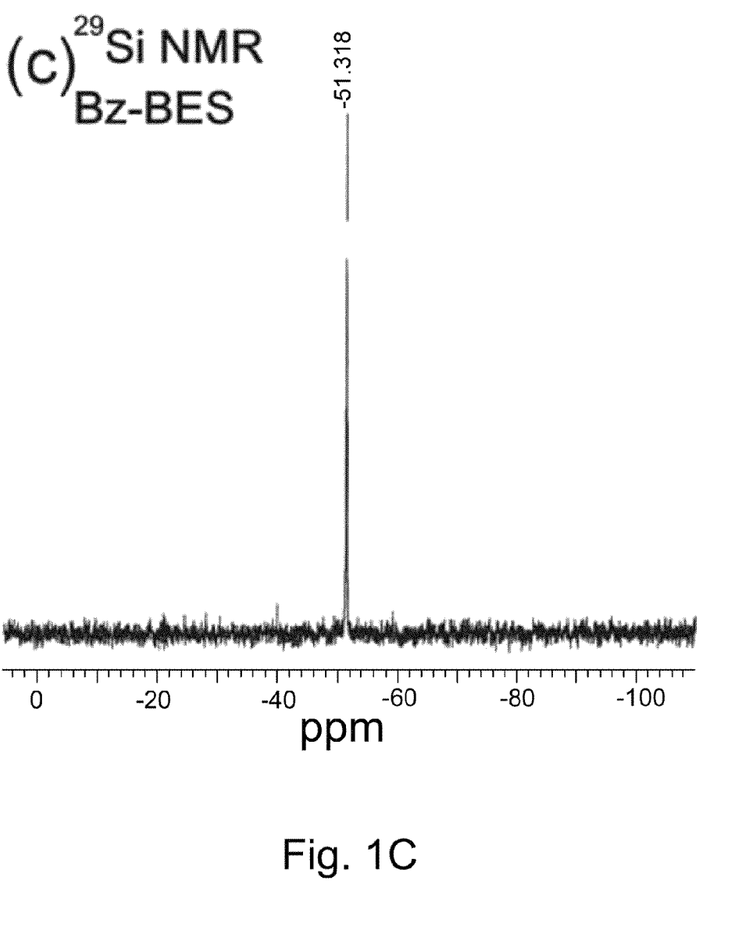
FIG. 1C is the view showing the $^{29}$Si NMR spectrum of Bz-BES.

Through analyzing spectrums of Fourier transform infrared radiation (FTIR) shown in FIG. 1A, specific absorption peaks for Bz-BES appear at 1231 cm$^{-1}$ and 1021 cm$^{-1}$ (stretching C—O—C of benzoxazine); at 1498 cm$^{-1}$ (tri-substituted phenyl group); and at 1100 cm$^{-1}$ (Si—O—C). Through analyzing a spectrum of $^1$H nuclear magnetic resonance (NMR) shown in FIG. 1B, specific resonance peaks for Bz-BES appear at δ=4.83 ppm (O—CH$_2$—N) and δ=3.93 ppm (Ph-CH$_2$—O). At the same time, trough analyzing the $^1$H NMR spectrum, other specific resonance peaks for Bz-BES appear at δ=0.67 ppm (Si—CH$_2$—), at δ=1.22 ppm (Si—OCH$_2$CH$_3$), at δ=1.59 ppm (—CH$_3$ in BPA), at δ=1.68 ppm (Si—CH$_2$CH$_2$—), at δ=2.74 ppm (N—CH$_2$—), at δ=3.82 ppm (Si—OCH$_2$CH$_3$) and at δ=6.66~6.93 ppm (aromatic proton). Except the above specific resonance peaks, Bz-BES shows no other resonance peaks at the chemical shift around 3.0~3.5 ppm in the $^1$H NMR spectrum. Hence, through the spectrum analysis, ring-opening benzoxazine groups do not appear in the products. Besides, in a $^{29}$Si NMR spectrum, only one resonance peak for Bz-BES appears at about δ=−51.3 ppm in FIG. 1C. Comparing to a specific resonance peak for APTES at δ=−46.3 ppm, the resonance peak for Bz-BES is obviously shifted. This also shows that Bz-BES has a different structure to the reactant APTES. The single peak in spectrum also shows high purity of the product Bz-BES. During fabricating Bz-BES, no Si—OEt hydrolysis happens. The molecular weight of Bz-BES of 717.8 g mol$^{-1}$ coincides with a figured-out value of 718 g mol$^{-1}$ (C$_{37}$H$_{62}$N$_2$O$_8$Si$_2$).

In reactions of hydrolysis and condensation, Bz-BES is used as a starting material to obtain xerogel through sol-gel. Kinds and densities of the catalysts have great influence on gel time. In the reactions of hydrolysis and condensation, acid (HCl) or basic (NaOH) catalysts can be used. When 0.2N NaOH water solution is used, the gel time is about 96 hrs. In the other hand, when 0.2N HCl water solution is used, no gelation will happen even after 1 month. This phenomenon is very similar to what have been reported concerning alkyl- and aryl-bridged polysilsesquioxanes, but contrast to what have been reported concerning bisimide-bridged polysilsesquioxane. When an NaOH catalyst having a density higher than 0.4N is used, the gel time in the sol-gel system for Bz-BES is shortened to 3 hrs. Then, the obtained gel product is washed by THF and distilled water. After vacuum dried at a room temperature, xerogel of Bz-BES (XG-Bz-BES) is obtained. In the FTIR spectrums, a broad absorption peak of Si—O—Si and an absorption peak of CH for XG-Bz-BES appear at about 1000-1100 cm$^{-1}$ and about 2900 cm$^{-1}$, respectively. All these show sol-gel of Bz-BES as in FIG. 1A.

A further thermal treatment to XG-Bz-BES forms cured polybenzoxazine-bridged polysilsesquioxanes (PBz-BPSSQ). In the thermal treatment, a ring-opening polymerization is processed to benzoxazine group to form a cross-linked polybenzoxazine network. Moreover, condensation may happen to residual silanol groups to increase a condensation degree of polysilsesquioxanes having benzoxazine-containing group.

Figure 2:
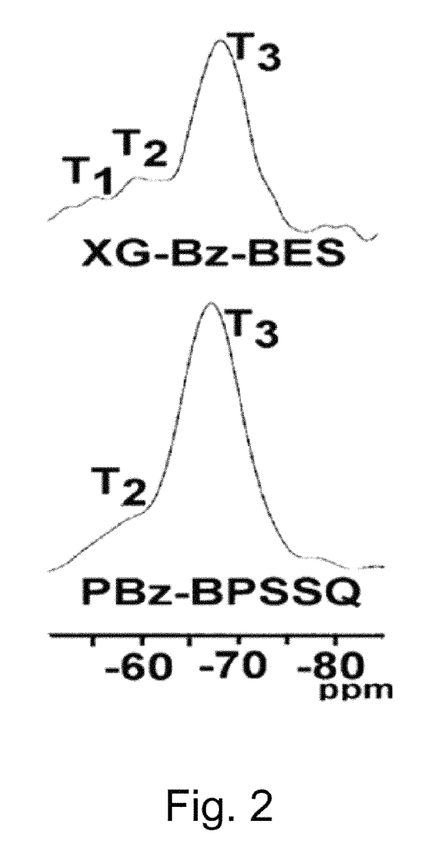
FIG. 2 is the view showing the solid $^{29}$Si NMR spectrums of XG-Bz-BES and PBz-BPSSQ.

In the solid $^{29}$Si NMR spectrums shown in FIG. 2, each of XG-Bz-BES and PBz-BPSSQ has a resonance peak at about δ=−67.0 ppm, which coincides with the resonance peak for condensed silicon (T$_3$). Corresponding resonance peaks for T$_2$ and T$_1$ appear at about δ=−58.5 ppm and δ=−54.2 ppm. Comparing to PBz-BPSSQ, the strengths of the resonance peaks for T$_2$ and T$_1$ are a lot weaker. This also shows the appearance of condensation of silanol group in the thermally treatment. The above polymerization of benzoxazine group also forms tetra-substituted phenyl group. Through analyzing an FTIR spectrum of the tetra-substituted phenyl group, an absorption peak is found at about 1485 cm$^{-1}$. For comparison, the tri-substituted phenyl group has an absorption peak at about 1498 cm$^{-1}$ in the FTIR spectrum (as shown in FIG. 1A).

Figure 3:
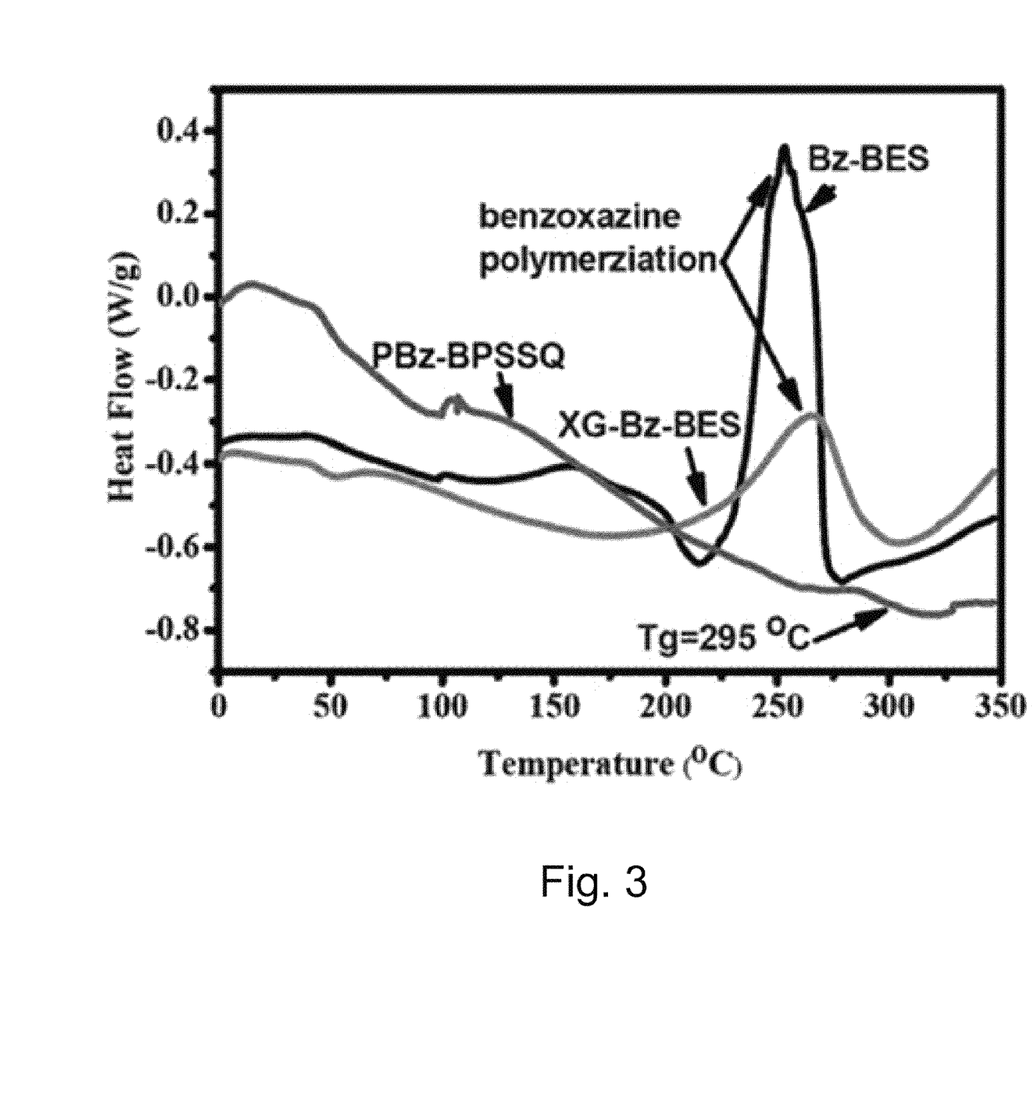
FIG. 3 is the view showing the DSC thermal spectrums of Bz-BES, XG-Bz-BES and PBz-BPSSQ.

Reaction on the benzoxazine group of Bz-BES is traced through DSC in FIG. 3. Bz-BES shows an exothermic peak. The above exothermic effect is related to thermo-induced ring-opening reaction of the benzoxazine group of Bz-BES. A center of the exothermic peak is at about 253° C. and the reaction enthalpy is about 170 J g$^{-1}$. Values of the reaction temperature and the enthalpy are quite close to what have been reported concerning benzoxazine. The polymerization of benzoxazine has the same exothermic peak as XG-Bz-BES. Comparing to Bz-BES, the exothermic peak of XG-Bz-BES is shifted to a higher temperature and the reaction enthalpy is shifted to a lower value. The above differences on the temperature and enthalpy may be owing to a steric hindrance formed by a polysilsesquioxanes network in XG-Bz-BES. After the thermal treatment, no exothermic peak appears in the DSC thermal spectrum of PBz-BPSSQ thus obtained. Thus, during the thermal treatment, polymerization is happened to the benzoxazine group of XG-Bz-BES with a high conversion ratio. What is noteworthy is that PBz-BPSSQ has a glass transition temperature at about 295° C., which shows a highly cross-linked benzoxazine network structure.

Figure 4A:
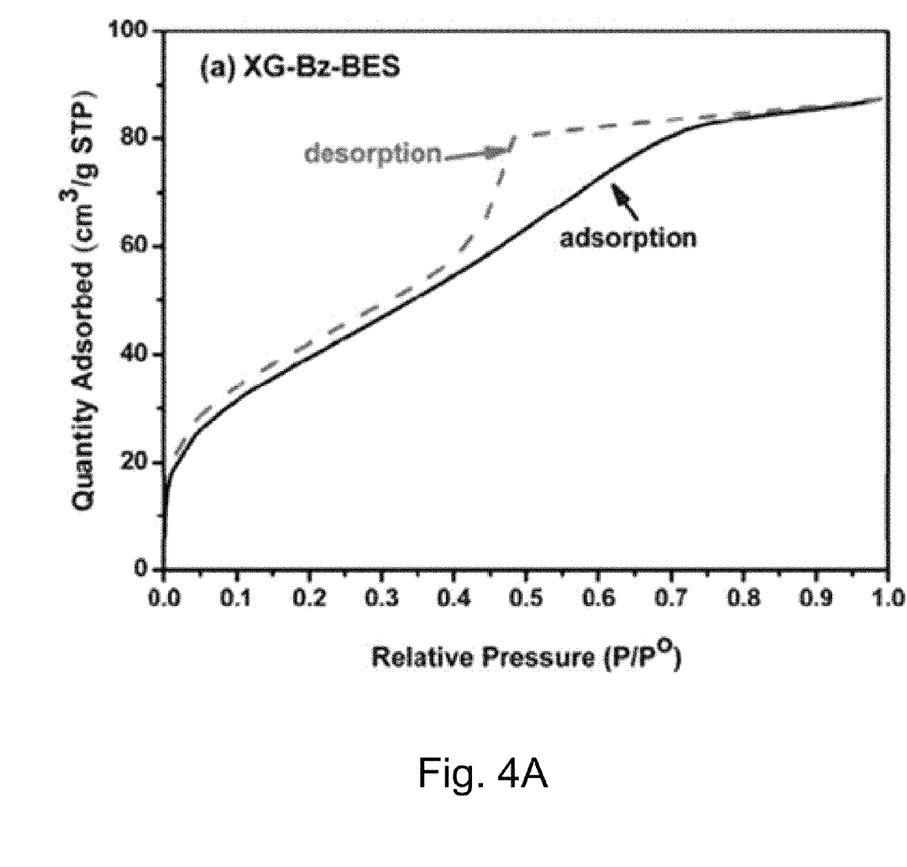
FIG. 4A is the view showing the nitrogen adsorption/desorption isotherms of XG-Bz-BES.
Figure 4B:
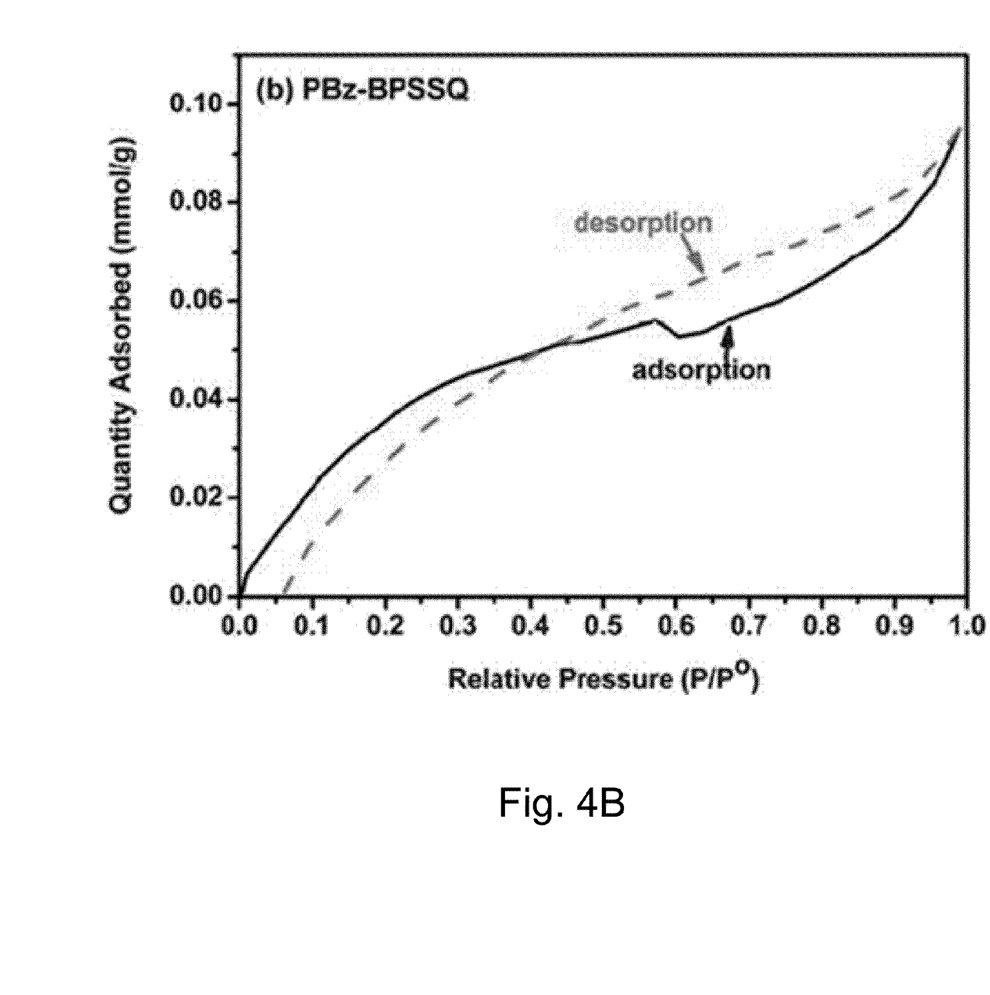
FIG. 4B is the view showing the nitrogen adsorption/desorption isotherms of PBz-BPSSQ.

In FIG. 4, XG-Bz-BES has a 144.0 m$^2$ g$^{-1}$ surface area and is a porous material having an average pore size about 3.7 Nm. The rigid benzoxazine-bridged structure helps preventing pore collapse and maintaining the porous structure of XG-Bz-BES during processes of gel reaction, drying, etc. A great amount of the cross-linked structure is formed in PBz-BPSSQ during polymerization of the benzoxazine group to induce pore collapse in the organic domain of PBz-BPSSQ. Thus, the surface area of PBz-BPSSQ is obviously decreased to 4.0 m$^2$ g$^{-1}$. The small surface area of PBz-BPSSQ also shows a relatively denser highly cross-linked benzoxazine domain.

Under 1 million hertz (MHz), PBz-BPSSQ has a dielectric constant about 1.57. Comparing to other dielectric constants of bridged polysilsesquioxanes, PBz-BPSSQ has a relatively lower dielectric constant, obviously. PBz-BPSSQ has a lower porosity in an organic polybenzoxazine domain. Such a lower porosity would not decrease the dielectric constant. A dielectric constant of hybrid polysilsesquioxane will be decreased following decreasing of the organic content. Hence, the decreasing of the dielectric constant of PBz-BPSSQ may be owing to the polysilsesquioxanes structure. However, the dielectric constant of PBz-BPSSQ is lower than what have been reported concerning bridged polysilsesquioxanes (~1.8 for 1 MHz).

On the other hand, for fabricating low-k cross-linked resins, Bz-BES is an effective cross-linking additive. By using Bz-BES and BPA-FBZ (50/50% weight percent) as precursors, a nano-composite of PBz-BPSSQ/PBz can be fabricated.

Figure 5A:
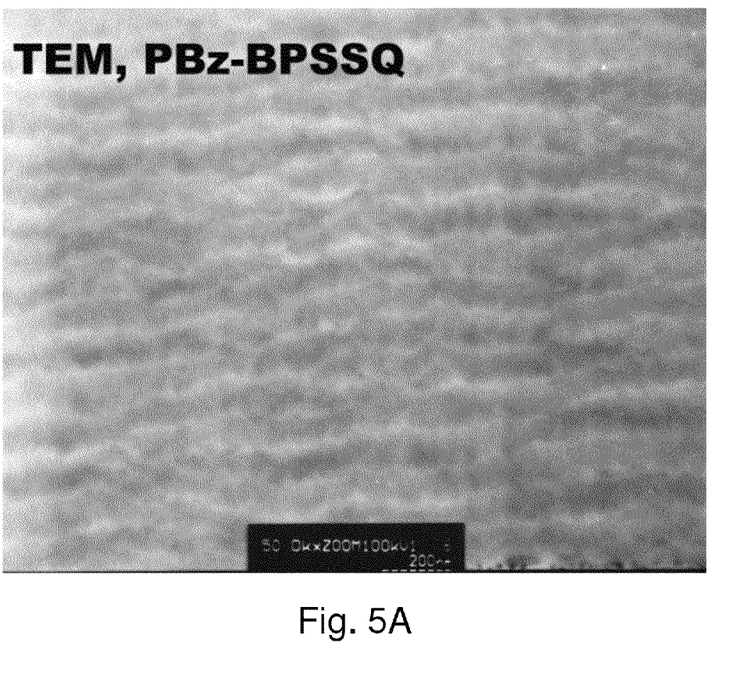
FIG. 5A is the view showing the TEM micrograph of PBz-BPSSQ.
Figure 5B:
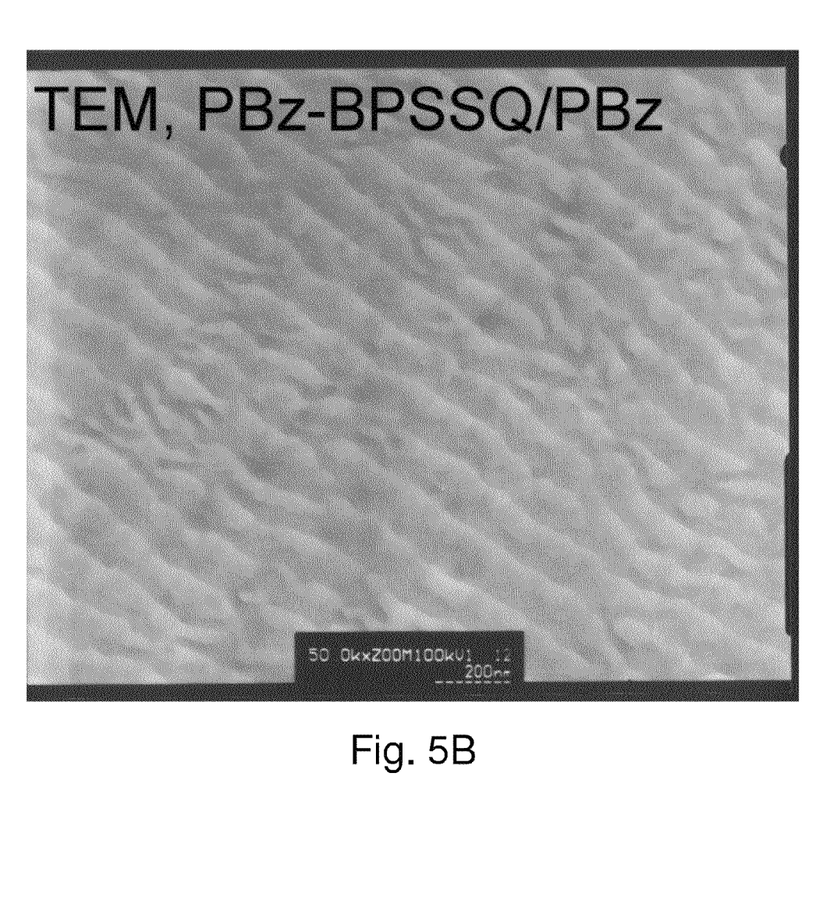
FIG. 5B is the view showing the TEM micrograph of PBz-BPSSQ/PBz.

In FIG. 5, a self-assembled layers structure is found in PBz-BPSSQ/PBz through transmission electron microscopy (TEM). The dark domain will be decreased following the decreasing of BPSSQ content in PBz-BPSSQ/PBz. As a result, a dielectric constant of PBz-BPSSQ/PBz is about 1.73. Such a value is higher than the dielectric constant of PBz/BPSSQ and is relatively lower than the dielectric constants of thermosets.

For a low-k dielectric material, mechanical strength is an important property. For a porous material, increasing porosity of the dielectric material can obviously decrease the dielectric constant of the porous material. However, a high porosity will greatly reduce modulus of the dielectric material. What is noteworthy is that Young's modulus of PBz-BPSSQ is about 3.1 GPa. Hence, comparing to a 1.85 k value and a 1.1 GPa Young's modulus for methylsilsesquioxane (MSSQ), PBz-BPSSQ has a more excellent mechanical strength.

Accordingly, benzoxazine is a hetero cyclic group, which can easily form a strong intermolecular hydrogen bond. The hydrogen bond helps forming self-assembled bridged polysilsesquioxanes. Besides, the benzoxazine group can process a ring-opening addition polymerization in the thermal treatment. The polymerization of the bridged groups helps control orientations of organic fragments in the bridged polysilsesquioxanes.

The present disclosure synthesizes a compound of benzoxazine-bridged bis(triethoxysilane) at first. Then, through sol-gel and thermal treatment, cross-linked polybenzoxazine-bridged polysilsesquioxane is fabricated. By observing the benzoxazine-bridged polysilsesquioxane materials, phase arrangements in the layer structures of polysilsesquioxanes can be found.

To sum up, the present disclosure is a bridged bis(alkoxysilane) or silsesquioxane compound having a benzoxazine-containing group, where the compound has a film network structure with a low dielectric constant and a high mechanical strength.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. A bridged bis(alkoxysilane) or silsesquioxane compound having a benzoxazine-containing group,
wherein said compound has a general structural formula as follows:

wherein X is selected from a group consisting of a chemical bond, —O—, —CH$_2$—, wherein $R^1$ and $R^3$ are two constituents selected from a group consisting of two of the same constituent and two different constituents;
wherein each of $R^1$ and $R^3$ is selected from a group consisting of $C_1$-type to $C_8$-type alkyl groups and $C_6$-type to $C_{15}$-type aryl groups; and
wherein m is an integer bigger than zero.

2. A bridged bis(alkoxysilane) or silsesquioxane compound having a benzoxazine-containing group,
wherein said compound has a specific structural formula as follows:

wherein X is selected from a group consisting of a CHEMICAL bond, —O—, —CH$_2$—, wherein $R^1$ and $R^3$ are two constituents selected from a group consisting of two of the same constituent and two different constituents;
wherein each of $R^1$ and $R^3$ is selected from a group consisting of $C_1$-type to $C_8$-type alkyl groups and $C_6$-type to $C_{15}$-type aryl groups; and
wherein m is an integer bigger than zero, wherein each of $R^2$ and $R^4$ is selected from a group consisting of two of the same constituent and two different constituents.

* * * * *